(12) United States Patent
Callahan et al.

(10) Patent No.: US 6,921,415 B2
(45) Date of Patent: *Jul. 26, 2005

(54) DEFORMABLE INTRAOCULAR CORRECTIVE LENS

(75) Inventors: Wayne B. Callahan, Roanoke, VA (US); Jeffrey S. Callahan, Antioch, TN (US)

(73) Assignee: ThinOptX, Inc., Abingdon, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/263,359

(22) Filed: Oct. 1, 2002

(65) Prior Publication Data

US 2003/0078655 A1 Apr. 24, 2003

Related U.S. Application Data

(60) Continuation of application No. 09/441,425, filed on Nov. 16, 1999, now Pat. No. 6,488,707, which is a division of application No. 08/914,767, filed on Aug. 20, 1997, now Pat. No. 6,096,077.

(51) Int. Cl.$^7$ .................................................. A61F 2/16
(52) U.S. Cl. ..................... 623/6.18; 623/6.25; 623/6.28
(58) Field of Search ............... 623/5.14, 5.15, 623/6.12, 6.16, 6.18, 6.25, 6.27, 6.28, 6.29, 6.3, 6.31, 6.54, 6.56; 351/160 R

(56) References Cited

U.S. PATENT DOCUMENTS

| | | |
|---|---|---|
| 4,102,567 A | 7/1978 | Cuffe et al. |
| 4,215,440 A | 8/1980 | Worst |
| 4,254,509 A | 3/1981 | Tennant |
| 4,573,998 A | 3/1986 | Mazzocco |
| 4,585,456 A | 4/1986 | Blackmore |
| 4,608,049 A | 8/1986 | Kelman |
| 4,624,669 A | 11/1986 | Grendahl |

(Continued)

OTHER PUBLICATIONS

*Hackh's Chemical Dictionary*, 4$^{th}$ Edition (1969) p. 232, 611, McGraw–Hill Book Co., New York City.

*Primary Examiner*—Paul B. Prebilic
(74) *Attorney, Agent, or Firm*—Waddey & Patterson, P.C.; Edward D. Lanquist, Jr.

(57) ABSTRACT

A deformable, artificial intraocular contact lens for implantation into the human eye to correct normal-vision problems. The lens may be positioned posteriorly from the iris, resting against the anterior surface of the posterior capsule's natural lens. Alternatively, the lens may be positioned in the anterior chamber of the eye. The implanted lens works in conjunction with the cornea and natural lens to provide proper vision, as a substitute for regular contact lens, spectacles, and radial keratotomy. The lens may be designed from a rigid or semi-rigid material. Due to the thinness of the structure, the lens may be rolled and inserted into the eye, minimizing both the length of the corneal incision and the stretching of the cornea.

5 Claims, 2 Drawing Sheets

U.S. PATENT DOCUMENTS

| | | |
|---|---|---|
| 4,655,775 A | 4/1987 | Clasby, III |
| 4,769,035 A | 9/1988 | Kelman |
| 4,795,462 A | 1/1989 | Grendahl |
| 4,816,032 A | 3/1989 | Hetland |
| 4,828,558 A | 5/1989 | Kelman |
| 4,834,750 A | 5/1989 | Gupta |
| 4,863,462 A | 9/1989 | Fedorov et al. |
| 4,932,970 A | 6/1990 | Portney |
| 4,950,290 A | 8/1990 | Kamerling |
| 4,994,080 A | 2/1991 | Shepard |
| 4,995,714 A | 2/1991 | Cohen |
| 5,002,568 A | 3/1991 | Katzen |
| 5,076,684 A | 12/1991 | Simpson et al. |
| 5,098,444 A | 3/1992 | Feaster |
| 5,100,226 A | 3/1992 | Freeman |
| 5,166,711 A | 11/1992 | Portney |
| 5,178,636 A | 1/1993 | Silberman |
| 5,192,319 A | 3/1993 | Worst |
| 5,229,797 A | 7/1993 | Futhey et al. |
| 5,236,452 A | 8/1993 | Nordan |
| 5,258,025 A | 11/1993 | Fedorov et al. |
| 5,476,512 A | 12/1995 | Sarfarazi |
| 5,476,514 A * | 12/1995 | Cumming .................. 623/6.37 |
| 5,480,428 A | 1/1996 | Fedorov et al. |
| 5,522,890 A | 6/1996 | Nakajima et al. |
| 5,549,670 A | 8/1996 | Young et al. |
| 6,083,261 A | 7/2000 | Callahan et al. ........... 623/6.38 |
| 6,096,077 A | 8/2000 | Callahan et al. |
| 6,152,958 A | 11/2000 | Nordan |
| 6,197,059 B1 | 3/2001 | Cumming |
| 6,224,628 B1 | 5/2001 | Callahan et al. ............. 623/6.4 |
| 6,488,707 B1 * | 12/2002 | Callahan et al. ........... 623/6.25 |
| 6,517,577 B1 | 2/2003 | Callahan et al. ........... 623/6.49 |
| 6,666,887 B1 * | 12/2003 | Callahan et al. ........... 623/6.25 |

* cited by examiner

DEFORMABLE INTRAOCULAR CORRECTIVE LENS

This application is a continuation application of U.S. patent application Ser. No. 09/441,425 filed Nov. 16, 1999, now U.S. Pat. No. 6,488,707, for "Method of Implanting a Deformable Intraocular Corrective Lens," which is hereby incorporated by reference, which is a divisional application of U.S. patent application Ser. No. 08/914,767 filed Aug. 20, 1997, now U.S. Pat. No. 6,096,077 for "Deformable Intraocular Corrective Lens," which is hereby incorporated by reference.

BACKGROUND OF THE INVENTION

1. Field of the Invention

The present invention relates to a deformable intraocular contact lens to correct vision problems, which lens is inserted into the eye anterior to the natural lens and has a functional design which minimizes cutting or stretching of the cornea to do so.

2. Description of the Related Art

Doctors trained in ophthalmology routinely surgically extract cataract-impaired lenses from patients' eyes and subsequently implant artificial lenses to prevent blindness. The artificial lens is typically manufactured from polymethylmethacrylate (PMMA), an acrylic plastic. PMMA is a preferred material because it is biologically compatible with the tissue of the eye, and it does not degrade over time.

Over the last 50 years, the success rate for implanting these intraocular lenses has improved to the point that surgeons now want to implant intraocular contact lenses anterior to the natural lenses to correct common vision problems, such as myopia (near-sightedness), hypermetropia (far-sightedness), and astigmatism (aberration in the convexity of the optic lens or cornea). However, using an intraocular lens for vision correction is currently problematic. In order to insert an intraocular lens, an incision of approximately 10 mm is made through the cornea or sclera. The new lens is passed through the incision into the anterior chamber of the eye. The inserted lens is then positioned over the pupil and anchored either anteriorly to or posteriorly from the iris. Unfortunately, the making of the incision causes astigmatism of the cornea.

Experience from cataract surgeries shows that the astigmatism will be reduced if a smaller incision is made. It follows that if the lens could be manipulated through a smaller incision, it will reduce the severity of the astigmatism. The optical portion of the intraocular lens, though, must have a diameter of at least approximately 6 mm in order to properly cover the pupil. So, the only way to pass a lens through a smaller incision is to first fold the lens into a U-shape or roll it so that the opposite edges are overlapping. However, currently designed PMMA lenses are rigid and too brittle to be rolled or folded. While it is known that a material which is rigid at a given thickness may be flexible at a lesser thickness, the maximum material thickness under which PMMA is flexible is approximately 0.25 mm. This thickness is too thin for use in a conventional contact lens because of the lens' optics requirements.

A lens has a convex lenticular surface into which incident light passes. The lens also has a posterior surface, opposite the lenticular surface, from which the refracted light exits. The posterior surface may be convex, planar or concave. The power of the lens is determined by the curvature of the lenticular and posterior surfaces. Because the optical portion of the contact lens is approximately 6 mm wide and the thickest portion is at the center of the lens, a conventional lens having a maximum thickness of under 0.25 mm at its center in order to be rolled cannot possess the requisite curvature to be optically useful.

Alternative lens materials are also currently used for the replacements of the natural lenses of cataract patients. One such alternative lens material is an acrylic that has a lower molecular weight than PMMA. This lower-weight acrylic lens is softer than PMMA so it can be folded in a U-shape. However, if not handled very carefully, the lower-weight acrylic will crease, rendering it unusable. In addition, the material is soft enough to adhere to itself if it is rolled or folded far enough to allow overlapping.

Another alternative lens material is silicone, the same material that is used in breast implants. The silicone collects protein in some patients, giving a yellow appearance and reducing the passage of light. The protein can become so dense as to create the appearance of a secondary cataract, significantly reducing the patient's ability to see. This is usually a lesser concern for cataract patient, when compared to the blindness which would result from the cataract. Also, most cataract patients tend to be elderly so the protein build-up might not advance too far during their lifetimes. For some cataract patients, though, the protein build-up necessitates that the silicone lens be removed and replaced. Because of the problems associated with protein build-up, silicone cannot be used to make long-term intraocular contact lenses for implantation into younger persons.

Two inventions for a deformable intraocular lens are set forth in U.S. Pat. No. 4,573,998 issued March 1986, to Mazzocco; and U.S. Pat. No. 5,522,890 issued June 1996, to Nakajima et al. These inventions employ a lens made of a molded elastic material. They do not suggest the use of PMMA.

Other inventions generally related to the art of optical lenses include: U.S. Pat. No. 4,254,509 issued March 1981, to Tennant (Accommodating Intraocular Implant); U.S. Pat. No. 4,585,456 issued April 1986, to Blackmore (Corrective Lens for the Natural Lens of the Eye); U.S. Pat. No. 4,655,775 issued April 1987, to Clasby (Intraocular Lens with Ridges); U.S. Pat. No. 4,769,035 issued September 1988, to Kelman (Artificial Lens and the Method for Implanting Such Lens); U.S. Pat. No. 4,795,462 issued January 1989, to Grendahl (Cylindrically Segmented Zone of Focus Artificial Lens); U.S. Pat. No. 4,816,032 issued March 1989, to Hetland (Arrangement in an Intraocular Anterior Chamber Lens); U.S. Pat. No. 4,950,290 issued August 1990, to Kamerling (Posterior Chamber Intraocular Lens); U.S. Pat. No. 4,994,080 issued February 1991, to Shepard (Optical Lens Having at Least One Stenopaeic Opening Located in the Central Area Thereof); U.S. Pat. No. 5,076,684 issued December 1991, to Simpson et al. (Multi-Focal Diffractive Ophthalmic Lenses); U.S. Pat. No. 5,098,444 issued March 1992, to Feaster (Epiphakic Intraocular Lens and Process of Implantation); U.S. Pat. No. 5,166,711 issued November 1992, to Portney (Multifocal Ophthalmic Lens); U.S. Pat. No. 5,229,797 issued July 1993, to Futhey et al. (Multifocal Diffractive Ophthalmic Lenses); U.S. Pat. No. 5,258,025 issued November 1993, to Fedorov et al. (Corrective Intraocular Lens); U.S. Pat. No. 5,480,428 issued January 1996, to Fedorov et al. (Corrective Intraocular Lens). None of these inventions solves the above-disclosed problems associated with currently known deformable intraocular lenses.

Thus, a need exists for a deformable intraocular contact lens which requires a minimal incision through the cornea, but does not possess the drawbacks associated with the currently known, alternative lens materials. None of the above inventions and patents, taken either singularly or in combination, is seen to describe such a lens as is achieved by the instant invention as claimed.

SUMMARY OF THE INVENTION

The present invention is a deformable intraocular contact lens constructed from PMMA for rolled or folded insertion into the human eye to correct common vision problems. The PMMA is deformable because all portions of the lens are manufactured to a thickness which is within a predetermined range of thicknesses. More particularly, at the first end of the range, the thickness of the lens is less than a maximum material thickness, the threshold under which the PMMA is flexible. At the second end of the range, the thickness of the lens is also greater than a minimum material thickness, the threshold above which the lens material will retain its pre-flexed shape subsequent to flexing. The novel design also enables the deformable PMMA lens to possess any desired convexity or concavity which would be required for vision correction. Of course, the deformable lens of the present invention may also be constructed from any other biologically compatible material that can be manufactured thinner than a pre-determined maximum material thickness to be rolled or folded for passage through a small incision in the cornea or sclera. The improved lens replaces the need for spectacles, contact lenses or radial keratotomy.

The intraocular contact lens has an anterior convex lenticular surface. The posterior surface of the lens comprises a planar, central disk which is surrounded by a series of concentric, planar, annular rings of increasing diameter. The annular rings are parallel to each other and to the central disk. The central disk and annular rings are also perpendicular to a radial axis passing though the apex of the lenticular surface. In combination, the central disk and the series of annular rings form a series of steps extending radially from the disk across the posterior surface to maintain a close proximity to the lenticular surface.

The thickness of the lens between the central disk of the posterior surface and the apex of the lenticular surface must be less than a predetermined maximum thickness. The predetermined maximum thickness is the thickness under which the material may be rolled or folded without exceeding the elastic limit of the selected lens material. For a lens constructed of PMMA, the maximum thickness between the posterior surface and the apex of the lenticular surface should be less than or equal to 0.25 mm.

The thickness of the lens at the periphery of the central disk must be greater than a pre-determined minimum thickness. The predetermined minimum thickness is the thickness above which the lens material will retain its pre-flexed shape subsequent to flexing. The minimum thickness is determined by the manufacturing process and the strength of the lens material. For PMMA, the minimum thickness between the lenticular surface and the periphery of the central disk should be greater than or equal to 0.0125 mm.

The radial width of the central disk of the posterior surface also falls within a predetermined range. The thicker the lens is at its apex, the farther the radial width may extend before the periphery of the central disk approaches the predetermined minimum thickness. The specific range of radial widths is determined by both the convexity of the lenticular surface and the thickness of the lens at its apex.

Similar to the central disk, the thickness between the lenticular surface and the posterior surface of the lens at the internal diameter of each annular ring should be less than or equal to the predetermined maximum thickness. The thickness between the lenticular surface and the posterior surface of the lens at the external diameter of each annular ring should be greater than or equal to the predetermined minimum thickness. The radial width of the annular rings will be within a predetermined range of lengths which is determined by the convexity of the lenticular surface and the thickness of the lens at the internal diameter of the annular ring. The greater the thickness of the lens at the internal diameter of the annular ring, the greater the radial length may be extended before the exterior diameter approaches the predetermined minimum thickness.

If an imaginary line is drawn to connect the posterior surface's internal diameters of the annular rings and the center of the central disk, the imaginary line will form an arc or parabola, depending on the various thicknesses chosen. This imaginary line forms the effective posterior surface. By changing the thicknesses and widths of the central disk and annular rings, the effective posterior surface may be shaped as desired. This is particularly relevant for applications in which the implanted lens is implanted posterior from the iris, as further described below. This is because the effective posterior surface may thereby be constructed in a predetermined shape which enables the implanted lens to be properly rested against the anterior surface of the natural lens capsule.

In one alternate embodiment of the invention, the central disk and annular rings of the posterior surface are not planar. Rather, each surface of the central disk and annular rings is convex. In a second alternate embodiment of the invention, each surface of the central disk and annular rings is concave. Thereby, particular degrees of convexity or concavity of each section of the posterior surface may be chosen to further help obtain particular focusing powers for different lenses. Also, in any of these embodiments, the central portion and annular rings of the lens may be of a symmetric or asymmetric ovular shape for correction of astigmatisms.

The periphery of the optical portion comprises a parallel lenticular area. The parallel lenticular area is of uniform thickness. The parallel lenticular area prevents the phenomenon known as edge effects which occurs if the optical portion of the lens does not adequately cover the periphery of the pupil. The edge effects are produced in various situations including when overhead lights are illuminated in low lighting situations, such as in roadway tunnels.

An anchoring means is attached to the optical portion to securely position the deformable intraocular contact lens anteriorly to the natural lens of the eye. The contact lens also has a non-optical transition area interconnecting the anchoring means to the optical portion of the lens. The transition area has a thickness of approximately 0.025 mm. The anchoring means comprises a pair of haptic fingers extending from the transition area and circumvolving the optical lens. The thickness of the haptic fingers is preselected to provide the optimal combination of strength and flexibility. Preferably, the thickness of each of the haptic finger is approximately 0.076 mm. The outer circumference of the haptic finger comprises the haptic edge. The haptic edge of the implanted lens is biased against the intraocular tissues. The thickness of the haptic edge is preselected to provide minimal stress to the eye tissues. Preferably, the thickness if the haptic edge is approximately 0.125 mm.

Once rolled and passed through the cornea, the implanted contact lens may be placed in either of two selected positions. Specifically, the implanted lens may be positioned anterior to the iris, in the anterior chamber of the of eye. If this position is chosen, the haptic edge of each of the haptic fingers will be biased against the trabeculum. Once positioned and allowed to unroll, the implanted lens will return to its original shape.

Alternatively, the implanted lens may be positioned posteriorly from the iris, and rest against the capsule of the natural lens of the eye. If this position is chosen, the haptic edge of each of the haptic fingers will be biased against the zonulas or ciliary sulcus. The implanted lens is able to be placed posteriorly from the iris because of the thinness of the implanted lens. The lens' thinness provides adequate clearance between the natural lens when at rest and the posteriorly positioned, implanted lens. The biconvex natural lens is in its most curved position when at rest. Contraction of the zonulas places tension on the capsule, flattening the curvature of the natural lens. Thus, with the implanted lens in position, the natural lens will continue to have the ability to change shape, without the possibility of injury arising from contact with the implanted lens.

Accordingly, it is a principal object of the invention to provide a deformable intraocular contact lens which requires a minimal incision through, or stretching of, the cornea for insertion.

It is another object of the invention to provide a deformable intraocular lens from a material such as PMMA which is biologically compatible with the eye tissue but will neither crease nor adhere to itself when rolled, nor cause eye disease as it ages.

It is a further object of the invention to provide an intraocular contact lens which may be positioned either anterior or posterior to the iris.

Still another object of the invention is to provide an intraocular lens for correcting common vision problems, such as myopia, hypermetropia, and astigmatism.

It is an object of the invention to provide improved elements and arrangements thereof in a deformable intraocular contact lens for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is a deformable intraocular lens constructed from a material which is biologically compatible with the eye tissues for correction of normal-vision problems.

Figure 1:
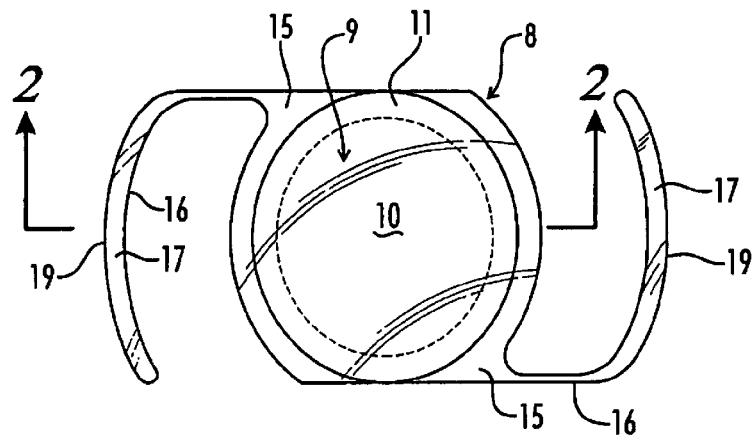
FIG. 1 is a top view of a deformable intraocular contact lens according to the present invention.

FIG. 1 is a top view of the deformable intraocular contact lens 8 according to the present invention. The deformable intraocular lens 8 is constructed of a material which is biologically compatible with the natural lens of the eye. The optical portion 9 of the lens 8 has an anterior convex lenticular surface 10. The periphery of the optical portion 9 comprises a parallel lenticular area 11. The parallel lenticular area 11 is of uniform thickness and is for preventing the phenomenon known as edge effects. A non-optical transition area 15 surrounds the parallel lenticular area 11. The anchoring means extend from the transition area 15. The anchoring means and anchor comprises a pair of haptic fingers 17 or anchors circumvolving the optical portion 9 of the deformable intraocular contact lens 8. Each of the pair of haptic fingers 17 have an outer circumferential haptic edge 19 for biasing against the tissue of the eye.

Figure 2:
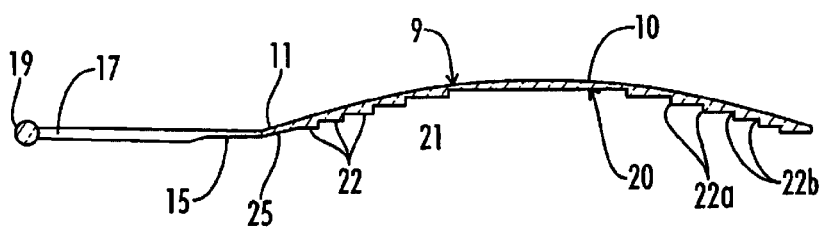
FIG. 2 is a cross-sectional view of the intraocular contact lens drawn along line 2—2.
Figure 3:
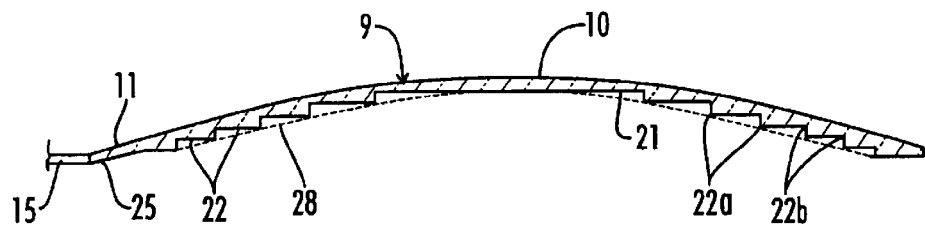
FIG. 3 is an enlarged, fragmented view of the optical portion and transition area of the lens depicted in FIG. 2.
Figure 4:
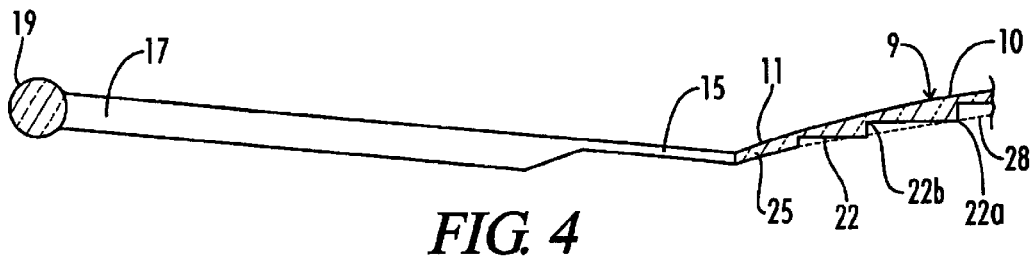
FIG. 4 is a fragmented view of the anchoring means and the transition area of the lens depicted in FIG. 2.

FIG. 2 is a cross-sectional view of the intraocular contact lens 8 drawn along line 2—2. FIG. 3 is a fragmented view of the optical portion 9 and transition area 15 of the lens 8 depicted in FIG. 2. FIG. 4 is a fragmented view of the anchoring means and the transition area 15 of the lens depicted in FIG. 2. These three figures depict, to varying degrees, the anterior lenticular convex surface 10 of the optic portion 9. The posterior surface 20 is also deoicted therein. The posterior surface 20 comprises a central disk 21 which is surrounded by a plurality of annular rings 22. The central disk 21 and series of annular rings 22 form a series of radial steps across the posterior surface 20 to maintain a close proximity to the lenticular surface 10. The thickness of the central disk 21 at the apex of the lenticular surface 10 is less than or equal to a predetermined maximum thickness so that the deformable intraocular contact lens 8 may be rolled without exceeding the elastic limit of the lens material. The thickness of the periphery of the central disk 21 is greater than or equal to a predetermined minimum thickness so that the deformable intraocular contact lens 8 will retain its pre-flexed shape subsequent to being rolled.

The surfaces of each annular ring 22 are planar and parallel with the central disk 21. Each annular ring 22 has an external point 22a and an internal diameter 22b. The thickness of the contact lens 8 between the external point 22a of the posterior surface's 20 annular rings 22 and the lenticular surface 10 is less than or equal to the predetermined maximum thickness. The thickness of the contact lens 8 between the internal diameter 22b of the posterior surfaece's 20 annular rings 22 and the lenticular surface 10 is greater than or equal to the predetermined minimum thickness. The outer most annular ring is adjacent to the posterior surface 25 of the parallel lenticular area 11.

FIG. 3 further includes a dashed line 28 depicting an imaginary line which connects the center of the central disk 21 and the edges internal diameters 21a of the annular rings 22 of the posterior surface 20. The imaginary line depicted by dashed line 28 is the effective posterior surface of the optical portion 9 of the deformable intraocular contact lens 8.

FIG. 2 through FIG. 4 further depict the parallel lenticular area 11 surrounding the periphery of the optical portion 9. The parallel lenticular area 11 is of uniform thickness and is for preventing edge effects. The transition area 15 surrounds the parallel lenticular area 11. The anchoring means extend from the transition area 15. FIG. 2 and FIG. 4 further depicts the anchoring means. The anchoring means comprises a pair of haptic fingers 17 circumvolving the optical portion 9 of the deformable intraocular contact lens 8.

Figure 5:
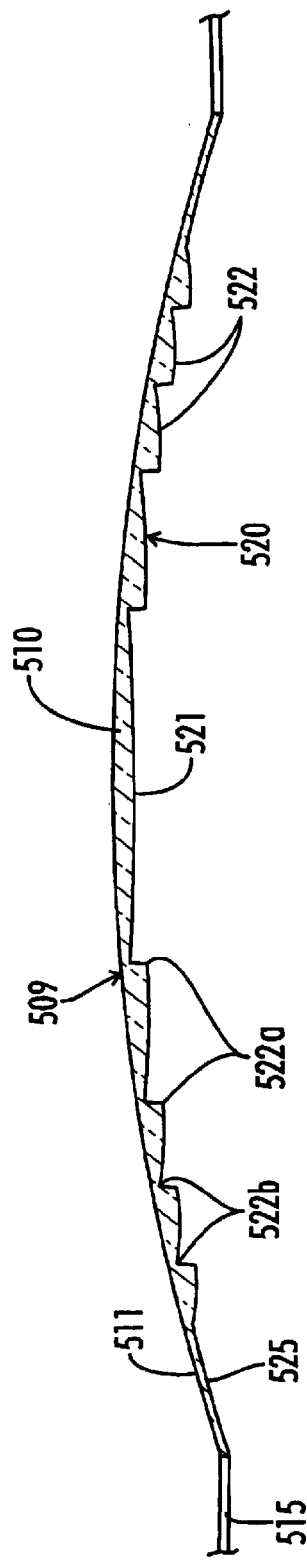
FIG. 5 is a cross-sectional fragmented view of a second embodiment of the invention.

FIG. 5 is a cross-sectional fragmented view of a second embodiment of the invention. In this alternate embodiment, the anterior lenticular surface 510 of the optic portion 509 is of the same convex shape as in the previously described embodiment. The posterior surface 520 comprises a central disk 521 which is surrounded by a plurality of annular rings 522. The central disk 521 and series of annular rings 522 form a series of radial steps across the posterior surface 520 to maintain a close proximity to the lenticular surface 510.

In this embodiment, the surfaces of the central disk 521 and each of the annular rings 522 are convex. The thickness of the central disk 521 at the apex of the lenticular surface 10 is less than or equal to the predetermined maximum thickness. The thickness of the periphery of the central disk 521 is greater than or equal to a predetermined minimum thickness.

Each annular ring 521 has an external point 522a and an internal diameter 522b. The thickness of the contact lens between the external point 522a of the posterior surface's 520 annular rings 522 and the lenticular surface 510 is less than or equal to the predetermined maximum thickness. The thickness of the contact lens between the internal diameter 522b of the posterior surface's 520 annular rings 522 and the lenticular surface 510 is greater than or equal to the predetermined minimum thickness. The parallel lenticular area 511 surrounds the periphery of the optical portion 509. The parallel lenticular area 511 is of uniform thickness. The transition area 515 surrounds the parallel lenticular area 511. The anchoring means (not shown) extends from the transition area 515. The outer most annular ring is adjacent to the posterior surface 525 of the parallel lenticular area 511.

Figure 6:
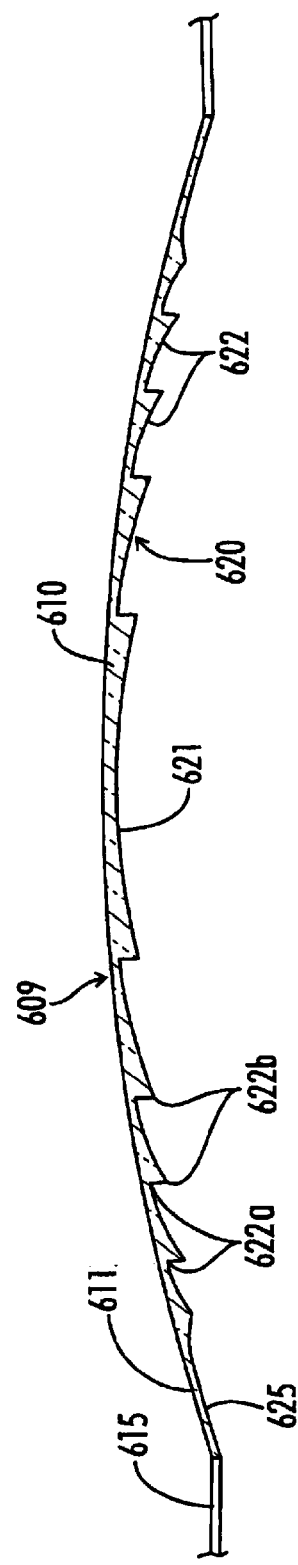
FIG. 6 is a cross-sectional fragmented view of a third embodiment of the invention.

FIG. 6 is a cross-sectional fragmented view of a third embodiment of the invention. In this alternate embodiment, the anterior lenticular surface 610 of the optic portion 609 is of the same convex shape as in the previously described embodiments. The posterior surface 620 comprises a central disk 621 which is surrounded by a plurality of annular rings 622. The central disk 621 and series of annular rings 622 form a series of radial steps across the posterior surface 620 to maintain a close proximity to the lenticular surface 610.

In this embodiment, the surfaces of the central disk 621 and each of the annular rings 622 are concave. The thickness of the central disk 621 at the periphery of the central disk 621 is less than or equal to the predetermined maximum thickness. The thickness of the lens between the apex of the lenticular surface 610 and the central disk 621 is greater than or equal to a predetermined minimum thickness.

Each annular ring 621 has an internal diameter 622a and an external point 622b. The thickness of the contact lens between the internal diameter 622a of the posterior surface's 620 annular rings 622 and the lenticular surface 610 is greater than or equal to the predetermined minimum thickness. The thickness of the contact lens between the external point 622b of the posterior surface's 620 annular rings 622 and the lenticular surface 610 is less than or equal to the predetermined maximum thickness. The parallel lenticular area 611 surrounds the periphery of the optical portion 609. The parallel lenticular area 611 is of uniform thickness. The transition area 615 surrounds the parallel lenticular area 611. The anchoring means (not shown) extends from the transition area 615. The outermost annular ring is adjacent to the posterior surface 625 of the parallel lenticular area 611.

It is to be understood that the present invention is not limited to the embodiments described above, but encompasses any and all embodiments within the scope of the following claims.

We claim:

1. A deformable intraocular corrective lens, comprising:
   a. an optical portion having a normal shape constructed of a material which is biologically compatible with the natural lens of the eye and for positioning anterior thereof, said optical portion having a predetermined maximum thickness of 0.25 mm under which the material may be rolled without exceeding the elastic limit of the material, said optical portion having a predetermined minimum thickness of 0.0125 mm above which the material retains said normal shape, wherein said deformable intraocular corrective lens is deformable for passage through a corneal incision having a length smaller than a diameter of the deformable intraocular corrective lens;
   b. said optical portion also having an anterior convex lenticular surface and a posterior surface, wherein said posterior surface comprises a central disk having a predetermined shape which is radially surrounded by a series of annular rings having a predetermined shape, said central disk and said series of annular rings forming a series of radial steps along said posterior surface; wherein an external point of an annular ring of said posterior surface and said anterior lenticular surface have a maximum separation of 0.1 mm; and
   c. an anchor attached to said optical portion, so that the optical portion is capable of attaching anteriorly to the natural lens of an eye through the anchor.

2. The deformable intraocular corrective lens of claim 1, wherein the predetermined shapes of the central disk and annular rings are planar, parallel to each other, and perpendicular to a radial axis passing through the apex of the lenticular surface.

3. The deformable intraocular corrective lens of claim 1, wherein the predetermined shapes of the central disk and annular rings are of a predetermined convexity for obtaining a particular focusing power.

4. The deformable intraocular corrective lens of claim 1, wherein the predetermined shapes of the central disk and annular rings are of a predetermined concavity for obtaining a particular focusing power.

5. The deformable intraocular corrective lens of claim 1, wherein the central disk and annular rings are radially asymmetric for correcting astigmatisms.

* * * * *